United States Patent
Mizutani et al.

(10) Patent No.: US 6,733,610 B2
(45) Date of Patent: May 11, 2004

(54) METHOD OF MAKING ABSORBENT ARTICLE EMPLOYING SURFACE LAYER WITH CONTINUOUS FILAMENT

(75) Inventors: Satoshi Mizutani, Kagawa (JP); Wataru Yoshimasa, Kagawa (JP); Megumi Tokumoto, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 155 days.

(21) Appl. No.: 09/939,222

(22) Filed: Aug. 24, 2001

(65) Prior Publication Data
US 2002/0049419 A1 Apr. 25, 2002

(30) Foreign Application Priority Data
Sep. 1, 2000 (JP) .................... 2000-265467

(51) Int. Cl.⁷ .................... A61F 13/15; A61F 13/00
(52) U.S. Cl. .................... 156/164; 156/160; 156/163; 156/229
(58) Field of Search .................... 156/160, 163, 156/164, 229, 244.11

(56) References Cited

U.S. PATENT DOCUMENTS

| | | |
|---|---|---|
| 3,367,333 A | 2/1968 | Scheier |
| 3,665,921 A | 5/1972 | Stumpf |
| 4,418,123 A * | 11/1983 | Bunnelle et al. ............ 156/164 |
| 4,891,258 A * | 1/1990 | Fahrenkrug ................. 428/138 |
| 5,334,176 A | 8/1994 | Buenger et al. |
| 5,611,791 A | 3/1997 | Gorman et al. |
| 5,705,249 A | 1/1998 | Takai et al. |
| 6,222,092 B1 | 4/2001 | Hansen et al. |

FOREIGN PATENT DOCUMENTS

| | | | |
|---|---|---|---|
| DE | 4422956 A1 | * | 1/1996 |
| EP | 0 429 802 A2 | | 6/1991 |
| EP | 0529641 A1 | * | 8/1992 |
| EP | 0 686 384 A2 | | 12/1995 |
| EP | 0 792 629 A2 | | 9/1997 |
| EP | 0953323 A1 | * | 11/1999 |
| EP | 0 976 375 A1 | | 2/2000 |
| GB | 2312625 A | * | 11/1997 |
| JP | 64-72744 A1 | | 3/1989 |
| JP | 10-245757 A1 | | 9/1998 |
| WO | WO 93/09741 A1 | | 5/1993 |
| WO | WO 95/15138 A1 | | 6/1995 |
| WO | WO 99/25286 A1 | | 5/1999 |
| WO | WO 99/27879 A2 | | 6/1999 |

* cited by examiner

Primary Examiner—Jeff H. Aftergut
(74) Attorney, Agent, or Firm—Darby & Darby

(57) ABSTRACT

Disclosed is an absorbent article having a liquid permeable surface layer, a backing sheet, and an absorbent layer interposed between the surface layer and the backing sheet. The surface layer includes a liquid permeable base and a layer of continuous filaments extending substantially in one direction and disposed on the surface of the base. The continuous filament layer is fixed to the base at a plurality of fixing portions which are spaced apart in the filament extending direction by a given pitch, to thereby form loop portions of the continuous filaments between adjacent fixing portions. The loop portions are raised toward the surface side.

3 Claims, 8 Drawing Sheets

METHOD OF MAKING ABSORBENT ARTICLE EMPLOYING SURFACE LAYER WITH CONTINUOUS FILAMENT

BACKGROUND OF THE INVENTION

1. Field of the Invention

The present invention relates to an absorbent article having a layer of continuous filaments disposed on a liquid receiving side to achieve good fitting feeling, and a manufacturing process thereof.

2. Description of the Related Art

Absorbent articles, such as sanitary napkin, disposable diaper or the like are typically of construction in which an absorbent layer is laid over a liquid impermeable backing sheet, and a liquid permeable surface material is laid over the liquid receiving side of the absorbent layer.

Conventionally, as the surface material of the absorbent article, use has been made of a non-woven fabric, such as a thermal bonded non-woven fabric in which thermoplastic synthetic fibers are bonded by hot embossing or by applying hot air, or a spun laced non-woven fabric in which fibers are entangled (interlaced) by applying water flow. With the fibers being bonded or entangled, these non-woven fabrics have a predetermined surface strength, while maintaining a sufficient bulkiness and permeability to liquid.

Moreover, as the surface material, it is also known in the art to use a synthetic film or non-woven fabric formed with a large number of through holes.

The surface material of the absorbent article is required to be excellent in liquid permeability to the absorbent layer, to have low possibility of causing so-called re-wetting back (the phenomenon in which the liquid once absorbed in the absorbent layer leaks back through the surface material to the surface of the absorbent article), and to be less irritative to the wearer's skin contacting with the surface material.

Irritation on the skin is affected by following ability of the material located on the surface of the surface material to motion of the skin. For example, the surface of the surface material formed of the porous film (i.e., the film formed with through holes) has low following ability to motion of the skin to possibly cause irritative feeling to the skin of a wearer.

On the other hand, the non-woven fabric provides relatively less irritation to the skin, because its fibers contacting with the wearer's skin may slightly move to follow the motion of the skin. In the nonwoven fabric formed with the through holes, too, since the fibers around the through holes may slightly move to follow the motion of the wearer's skin, it provides relatively less irritation to the skin. However, the absorbent article employing the surface material formed of a non-woven fabric is less effective in view point of re-wetting back prevention performance in comparison with the porous film.

As set forth above, neither the non-woven fabric nor the porous film could satisfy all the functions required for the surface material of the absorbent article. Therefore, it has been difficult to provide a surface material satisfying all the required functions.

SUMMARY OF THE INVENTION

The present invention has been worked out in view of the shortcoming in the prior art set forth above. Therefore, it is an object of the present invention is to provide an absorbent article which has a surface layer of a structure less irritative to the skin of a wearer and achieving high performance in restricting re-wetting back, and a manufacturing process therefor.

According to a first aspect of the invention, there is provided an absorbent article comprising: a liquid permeable surface layer; a backing sheet; and an absorbent layer interposed between the surface layer and the backing sheet, the surface layer including a liquid permeable base and a layer of continuous filaments extending substantially in one direction and disposed on the surface of the base, the continuous filament layer being fixed to the base at a plurality of fixing portions which are spaced apart in the filament extending direction by a given pitch, to thereby form loop portions of the continuous filaments between adjacent fixing portions, the loop portions being raised toward the surface side.

Preferably, the fixing portions are arranged in a pattern of rows each extending in the filament extending direction, wherein in any two rows adjacent in a direction perpendicular to the fiber extending direction, fixing portions in one row are not continuous to but are offset from fixing portions in the other row, so that peaks of loop portions in one row are offset from peaks of loop portions in the other row for permitting each individual loop portion to behave independently of others.

It is possible that pitches of the fixing portions are differentiated at different positions of the article, and heights of the loop portions are varied depending upon the pitches of the fixing portions. In this case, loop portions having a greater height may be arranged at a center portion in a liquid absorbing region of the absorbent article, and loop portions having a smaller height may be arranged at front and rear sides of the center portion and/or at left and right sides of the center portion.

It is also possible that loop portions having a greater height and loop portions having a smaller height are alternated in the filament extending direction.

It is further possible that each fixing portion is formed as a bent or curved fixing line, and a distance between two fixing lines adjacent in the filament extending direction varies depending upon a shape of the fixing lines, so that each loop portion per se varies in height at different positions thereof.

It is still further possible that the continuous filament layer is consisted of a plurality of rows of continuous filaments, each row extends in straight to have a predetermined width, and the rows are spaced apart in a direction perpendicular to the filament extending direction. In this case, the base is preferably a porous sheet.

Preferably, a height of the loop portion from the surface of the base is greater than a pitch between adjacent fixing portions defining the loop portion. Also preferably, between adjacent fixing portions, a total length of continuous filaments appearing on the outer surface of the loop portion is 1.1 to 4 times of the pitch of the fixing portions.

For example, the base is contracted in the filament extending direction after formation of the fixing portions, so that an initial pitch between adjacent fixing portions is shortened by contraction of the base into the given pitch for raising the loop portions.

For contraction of the base, the base may be formed of a stretchable material or a heat shrinkable material. Alternatively, the absorbent article may further comprise an elastic member fitted on the base for causing contraction.

According to a second aspect of the invention, there is provided a manufacturing process of an absorbent article having a surface layer, a backing sheet, and an absorbent layer interposed between the surface layer and the backing sheet, comprising the steps of:
(a) fitting a longitudinally stretched elastic member over one surface of a liquid permeable base;
(b) simultaneously with the step (a) or before or after the step (a), stacking a layer of continuous filaments extending substantially in one direction on the other surface of the base and fixing the continuous filament layer to the base at a plurality of fixing portions which are spaced apart in the filament extending direction by a given initial pitch;
(c) causing contraction of the base in the filament extending direction to shorten the given initial pitch into a given contracted pitch by releasing stretching force on the elastic member for raising the continuous filaments in each region between adjacent fixing portions from the surface of the base to form loop portions, and whereby forming the surface layer; and
(d) laminating the surface layer, the backing sheet on opposite surfaces of the absorbent layer for forming the absorbent article.

According to a third aspect of the invention, there is provided a manufacturing process of an absorbent article having a surface layer, a backing sheet, and an absorbent layer interposed between the surface layer and the backing sheet, comprising the steps of:
(a) longitudinally stretching a liquid permeable, stretchable base;
(b) simultaneously with the step (a) or after the step (a), stacking a layer of continuous filaments extending substantially in one direction on the base and fixing the continuous filament layer to the base at a plurality of fixing portions which are spaced apart in the filament extending direction by a given initial pitch;
(c) causing contraction of the base in the filament extending direction to shorten the given initial pitch into a given contracted pitch by releasing stretching force on the base for raising the continuous filaments in each region between adjacent fixing portions from the surface of the base to form loop portions, and whereby forming the surface layer; and
(d) laminating the surface layer, the backing sheet on opposite surfaces of the absorbent layer for forming the absorbent article.

According to a fourth aspect of the invention, there is provided a manufacturing process of an absorbent article having a surface layer, a backing sheet, and an absorbent layer interposed between the surface layer and the backing sheet, comprising the steps of:
(a) supplying a heat shrinkable base;
(b) stacking a layer of continuous filaments extending substantially in one direction on the base and fixing the continuous filament layer to the base at a plurality of fixing portions which are spaced apart in the filament extending direction by a given initial pitch;
(c) causing heat shrinkage of the base in the filament extending direction to shorten the given initial pitch into a given contracted pitch by applying a heat on the base for raising the continuous filaments in each region between adjacent fixing portions from the surface of the base to form loop portions, and whereby forming the surface layer; and
(d) laminating the surface layer, the backing sheet on opposite surfaces of the absorbent layer for forming the absorbent article.

The manufacturing processes as set forth above may further comprise a step of opening a tow which is a bundle of crimped continuous filaments for forming the continuous filament layer. In addition, the manufacturing processes may further comprise a step of spreading the continuous filament layer in its width direction to have a uniform bulk, after the step of opening.

BRIEF DESCRIPTION OF THE DRAWINGS

The present invention will be understood more fully from the detailed description given hereinafter and from the accompanying drawings of the preferred embodiment of the present invention, which, however, should not be taken to be limitative to the invention, but are for explanation and understanding only.

In the drawings.

DESCRIPTION OF THE PREFERRED EMBODIMENT

The present invention will be discussed hereinafter in detail in terms of the preferred embodiment of the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structure are not shown in detail in order to avoid unnecessary obscurity of the present invention.

Figure 1:
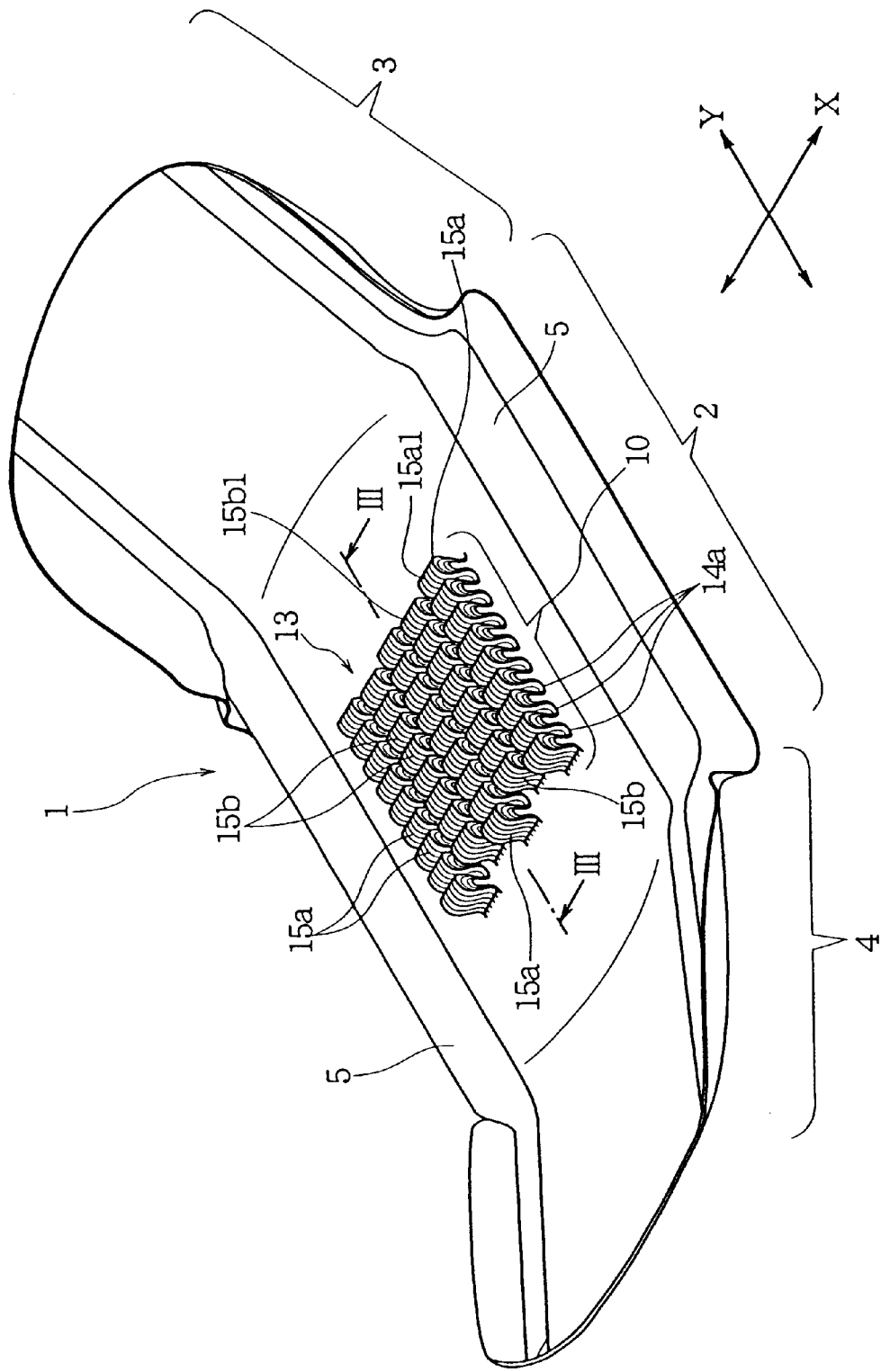
FIG. 1 is a perspective view showing an absorbent article according to a first embodiment of the present invention.
Figure 2:
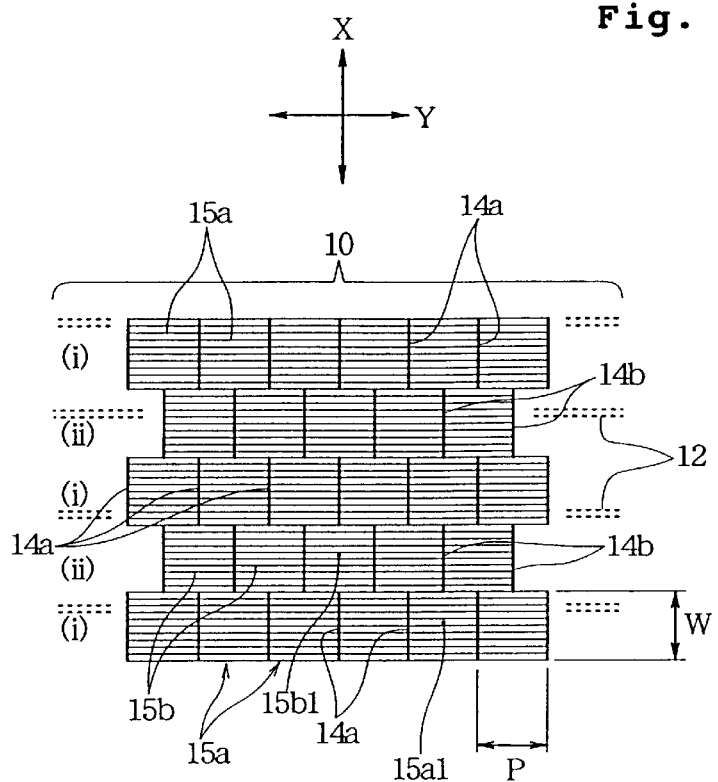
FIG. 2 is a plan view of a portion where a continuous filament layer is fixed to a base.
Figure 3:
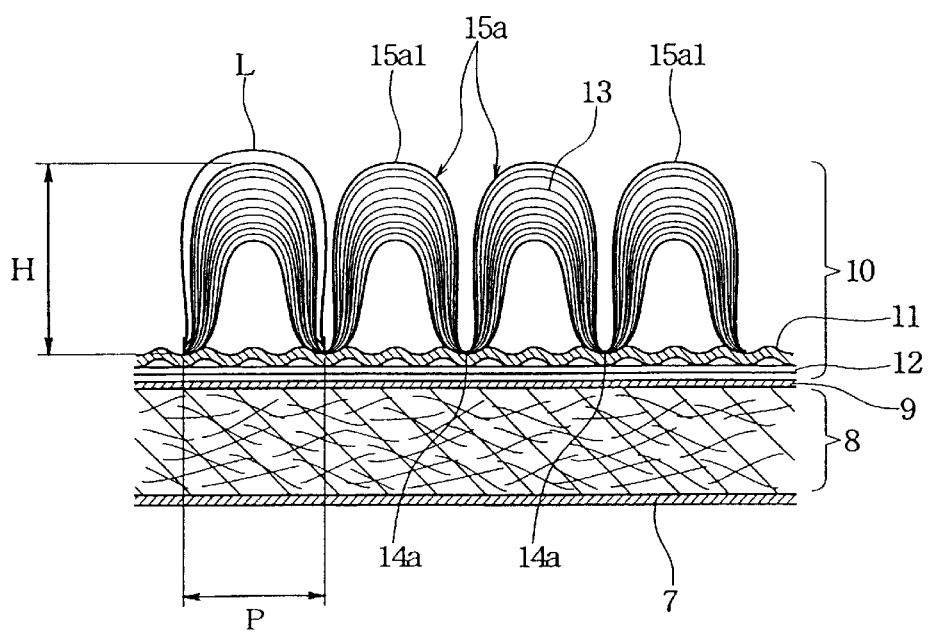
FIG. 3 is a section taken along line III—III of FIG. 1.
Figure 4:
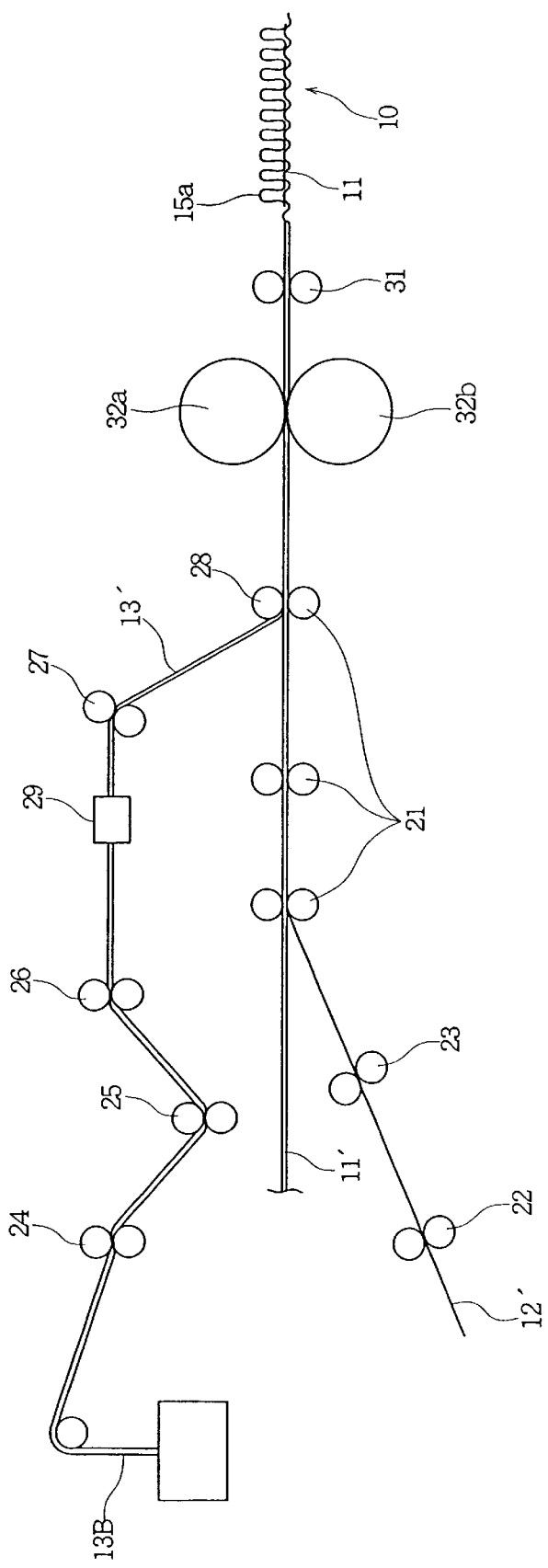
FIG. 4 is a diagrammatic illustration showing a manufacturing process of a surface layer of the absorbent article according to the first embodiment of the invention.

FIG. 1 is a perspective view showing an absorbent article according to a first embodiment of the present invention, FIG. 2 is a plan view of a portion where a continuous filament layer is fixed to a base, FIG. 3 is a sectional view of a portion of the absorbent article of FIG. 1, as taken along line III—III, and FIG. 4 is a diagrammatic illustration showing a manufacturing process of the absorbent article of FIG. 1.

An absorbent article 1 shown in FIG. 1 is a sanitary napkin. Throughout the disclosure and claims, a direction identified by an arrow x is referred to as width or lateral direction and a direction identified by an arrow Y is referred to as longitudinal direction. The absorbent article 1 has an intermediate portion 2, and a front portion 3 and a rear portion 4 located at opposite sides of the intermediate portion 2. On both side portions of a main body of the absorbent article 1, side leakage preventing walls 5 and 5 extending in the longitudinal direction are provided. To the side leakage preventing walls 5 and 5, elastic members are provided for applying elastic contractive force in the longitudinal direction. By the contractive force, the main body of the absorbent article 1 is bowed in the longitudinal direction (Y direction) and the side leakage preventing walls 5 and 5 are raised up from the liquid-receiving face of the main body, mainly at the intermediate portion 2, to form three-dimensional shape.

As shown in FIG. 3, the main body of the absorbent article 1 comprises a liquid impermeable backing sheet 7, an absorbent core (absorbent layer) 8, a liquid permeable surface sheet 9, and a liquid permeable surface layer 10, which are stacked upward in the order named above.

The absorbent core 8 is provided between the backing sheet 7 and the surface sheet 9 to extend over a part of the front portion 3, the intermediate portion 2, and a part of the rear portion 4 of absorbent article 1. In an outer peripheral region beyond the outline of the absorbent core 8, the backing sheet 7 and the surface sheet 9 are adhered to each other with a hot melt adhesive or fusion bonded (welded) to each other by hot embossing. The region where the absorbent core 8 exists is referred to as a liquid absorbing region.

At the center portion of the intermediate portion 2, namely at the center portion of the liquid absorbing region, the surface layer 10 is provided. The surface layer 10 is preferably formed in a size of 60 to 400 mm in the longitudinal direction (Y direction) and 10 to 80 mm in the width direction (X direction).

The backing sheet 7 is liquid impermeable and is formed from a water vapour permeable resin film, a non-woven fabric or a laminate of a resin film and a non-woven fabric. The surface sheet 9 is liquid permeable and is formed from a non-woven fabric fabricated by hydrophilic fibers or synthetic fibers treated to be hydrophilic, or a perforated non-woven fabric. The absorbent core 8 is formed by mixing crushed pulp and SAP (superabsorbent polymer), followed by wrapping the mixture in liquid permeable paper. In the alternative, the absorbent core 8 may also be formed from air laid pulp formed into a sheet by a binder process, absorbent paper, or a non-woven fabric primarily consisted of hydrophilic fibers.

The side leakage preventing wall 5 is formed from a non-woven fabric, such as through-air bonded non-woven fabric, point bonded non-woven fabric, spun bonded non-woven fabric, spun laced non-woven fabric, melt blown non-woven fabric, or air laid non-woven fabric.

In the surface layer 10, elastic members 12 are fixed (joined) on the back side of a liquid permeable base 11. Also, a layer 13 of continuous filaments is provided on the surface side of the base 11. These individual continuous filaments extend continuously in the longitudinal direction (Y direction). For example, the continuous filament layer 13 can be prepared by opening a bundle of crimped continuous filaments, called as tow.

This continuous filament layer 13 is disposed to have a substantially uniform bulkiness (thickness) over the entire area of the surface layer 10. The continuous filament layer 13 and the base 11 are fixed (joined) to each other at a plurality of fixing lines (fixing portions) 14a and 14b.

In the embodiment shown in FIGS. 1 to 3, all fixing lines 14a and 14b extend in straight in a direction perpendicular to the Y direction, along which the individual continuous filaments extend. Lengths W of the fixing lines 14a and 14b in the X direction are the same. The fixing lines 14a and 14b are aligned in the Y direction at equal pitch P to form respective rows. A plurality of rows are arranged in the X direction in side-by-side relationship. In FIG. 2, the rows of the fixing lines 14a are indicated at (i) and referred to as odd number rows; the rows of the fixing lines 14b are indicated at (ii) and referred to as even number rows. The fixing lines 14a and the fixing lines 14b are shifted relative with each other for half pitch P so that the fixing line 14b in the even number row (ii) is longitudinally located at the center between adjacent fixing lines 14a in the odd number row (i).

In the odd number row (i), continuous filaments located therein are protruded upwardly from the surface, between respectively adjacent fixing lines 14a, to form loop portions 15a. In the even number row (ii), too, continuous filaments located therein are protruded upwardly from the surface, between respectively adjacent fixing lines 14b, to form loop portions 15b.

In the shown embodiment, the loop portions 15a and 15b are formed in the following manner. At first, the elastic members 12 are fixed to the base 11 in a condition where each elastic member is stretched. Then, the continuous filament layer 13 is stacked on the surface of the base 11, and the fixing lines 14a and 14b are formed (i.e., the individual continuous filaments are fixed on the base 11 at selected points for forming the fixing lines 14a and 14b). Thereafter, force placing the elastic members 12 in stretched condition is released to permit contraction thereof. By contracting force of the elastic members 12, the base 11 is contracted in the longitudinal direction (Y direction) to shorten distances between adjacent fixing lines 14a and between adjacent fixing lines 14b for forming the loop portions 15a and 15b.

Between the fixing lines 14a in the odd number rows (i), the fixing lines 14b in the even number rows (ii) are located as set forth above. Therefore, the peak portions 15a1 of the loop portions 15a formed between respective fixing lines 14a and the peak portions 15b1 of the loop portions 15b formed between respective fixing lines 14b are arranged in staggered fashion. Also, the loop portions 15a in the odd number rows (i) and the loop portions 15b in the even number rows (ii) are located adjacent but independent with each other.

These individual loop portions 15a and 15b are formed from continuous filaments extending continuously in the Y direction. Moreover, the each continuous filament is fixed to the base 11 at a plurality of points (i.e., at the fixing lines 14a or 14b) distanced at the predetermined pitch P. Therefore, continuous filaments do not easily fall out of the base 11.

In the loop portions 15a and 15b, the individual continuous filaments are easily deformed in the Y direction and X direction. Therefore, the continuous filaments may follow movement of the wearer's skin to hardly cause irritation on the skin of the wearer. Particularly, since the loop portions 15a in the odd number row (i) and the loop portions 15b in the even number row (ii) adjacent with each other are mutually independent with each other, the continuous filaments in an independent region defined by adjacent fixing lines 14a and the continuous filaments in an independent region defined by adjacent fixing lines 14b may move individually at respective loop portions 15a and 15b. Accordingly, the continuous filaments may flexibly follow to the motion of the skin of respective portion of the wearer.

On the other hand, as shown in FIG. 3, in relation to the pitch P of the fixing lines, the height H of respective loop portions 15a and 15b are sufficiently large. A preferred range of the height H is 2 to 15 mm. By providing the height H greater than the pitch P, the loop portions 15a and 15b are enhanced in shape recovery properties. Specifically, even when the loop portions 15a and 15b are crushed by a vertical pressure (i.e., a force applied downward in Z direction perpendicular to X-Y plane), they can restore their original shape immediately after releasing of the pressure.

For enabling the continuous filaments forming respective loop portions 15a and 15b to follow motion of the skin of the wearer in the X direction and Y direction and to cause compressing deformation in response to vertical compression force, each of continuous filaments located at the outermost positions of the loop portions 15a and 15b preferably has a total length L between the fixing lines in a range greater than or equal to 1.1 times of the pitch P and less than or equal to 4 times of the pitch P.

For assuring independent behavior of the loop portions 15a and 15b of the continuous filaments formed between the fixing lines in the X direction and Y direction, it is preferred to set a difference between the pitch P of the fixing lines and the length W of the fixing lines as small as possible to make the top plan view of the loop portion 15a, 15b close to square as close as possible. Therefore, it is preferred that W/P or P/W is in a range of 0.5 to 1.5, and more preferably in a range of 0.8 to 1.2.

It is preferred that the continuous filaments have a fineness in a range of 1.1 to 8.8 dtex. Within this range, the continuous filaments forming the loop portions 15a and 15b may restore original condition after deformation in the X direction and Y direction, and may restore original loop condition after exertion of compressing force in the vertical direction. If the fineness of the continuous filaments is less than the range set forth above, the loop portions 15a and 15b should lack elastic restoration ability. On the other hand, when the fineness of the continuous filaments exceeds the range set forth above, the filaments should give stiff feeling to the wearer's skin.

Moreover, the continuous filaments as used herein are preferably crimped. In this case, individual crimped continuous filaments in respective loop portions 15a and 15b will be appropriately entangled one another while maintaining independency to some degree. Thus, in the loop portions 15a and 15b, individual filaments may have freedom in motion but are cooperative in elastic restoration.

In the crimping condition of the continuous filament, number of crimp of individual filament per 1 inch is preferably in a range of 5 to 40, and further preferably in a range of 5 to 30. Also, crimp modulus of elasticity of the continuous filament is preferably greater than or equal to 70%.

Number of crimp is based on JIS L-1015 and crimp modulus of elasticity is based on JIS L-1074. In case of the filament of a fineness less than 5.5 dtex, an initial load of 0.49 mN is applied in pulling direction, and in case of the filament of a fineness greater than or equal to 5.5 dtex, an initial load of 0.98 mN is applied in pulling direction. Number of crimp referred to is number of threads (peaks) per 1 inch (25 mm) when the initial load is applied.

On the other hand, the crimp modulus of elasticity is expressed by:

$$\{(b-c)/(b-a)\}\times 100 \ (\%)$$

wherein a is a length of filament when the initial load is applied, b is a length when the crimp is stretched by applying a tension force of 4.9 mN per 1.1 dtex for 30 seconds, and c is a length as applied the initial load again after 2 minutes from releasing of the tension force.

Also, a strength of the continuous filament layer 13 in the Y direction in the condition where continuous filaments are entangled by crimp is preferably greater than or equal to 0.14 N/inch. Here, the strength referred to is expressed by a load at break, when the layer of continuous filaments having a basis weight of 25 $g/m^2$ is formed in carding process, ten layers are laminated to form a test sample, the test sample is clamped to have a chuck-to-chuck distance of 100 mm by Tensilon tensile test machine, and chuck-to-chuck distance is increased at a speed (ratio) of 100 mm/min.

When the loop portions 15a and 15b are formed by such continuous filaments, soft touch to skin is achieved and each individual loop may move freely. Furthermore, such loop portions 15a and 15b may have superior elastic restoration ability.

In the absorbent article 1 employing the surface layer 10, when menstrual blood or the like is applied to the loop portion, it flows along the continuous filaments to reach the base 11 and then pass through the base 11 and the surface sheet 9 to be absorbed by the absorbent core 8.

The continuous filament layer 13 for use in the surface layer 10 having a property to infiltrate liquid, is preferred to have a basis weight of 20 to 200 $g/m^2$. If the basis weight is less than 20 $g/m^2$, number of continuous filament becomes too small to form a thick filament loop portion on the surface of the absorbent article 1. On the other hand, in case of the article, in which the continuous filament layer 13 is fixed on the base 11 by heat fusion, if the basis weight of the continuous filament layer 13 is less than the foregoing range, sufficient fixing strength cannot be obtained. On the other hand, if the basis weight is in excess of the foregoing range, capillary effect between the continuous filaments becomes excessively strong to cause retention of the liquid in the continuous filament layer 13 to provide wet feeling to the wearer.

The continuous filaments forming the continuous filament layer 13 are formed of heat-fusible hydrophobic synthetic resin so that they can be fusion bonded to the base 11. Examples of the continuous filaments include: mono-fibers such as those of PE (polyethylene), PP (polypropylene) or PET (polyethylene terephthalate); conjugated fibers of core-sheath structure, such as those of PE/PET or PE/PP; and conjugated fibers of side-by-side structure, such as those of PE/PET or PE/PP. The continuous filaments formed of synthetic resin are preferably treated to be hydrophilic with a hydrophilic agent being applied to their surfaces or kneaded in the resin. It is also preferred that the continuous filaments contain inorganic filler for whitening, such as titanium oxide or the like, in the content of 0.5 to 10% by weight. By whitening process, the continuous filaments may easily hide menstrual blood absorbed in the absorbent core 8 from external view. The individual continuous filaments may have a circular or modified cross-section.

Here, it is further possible to laminate hydrophilic fibers such as those of rayon on the continuous filament layer 13 of synthetic resin in a content of 5 to 30% by weight, or to bond mono-fibers such as natural cellulose fibers to the continuous filament layer 13 with an adhesive.

In an alternative, the continuous filament layer 13 may be formed from split yarns. Split yarns are prepared by splitting a film in a width direction to form filaments joined in net form.

The base 11 is preferably formed from a now-woven fabric of thermoplastic synthetic resin fibers for permitting thermal fusion with the continuous filament layer 13 and for obtaining fusion bonding strength. Examples of the non-woven fabric preferably include a point bonded non-woven fabric, a through-air bonded non-woven fabric, a spun bonded non-woven fabric, an air laid non-woven fabric and a spun laced non-woven fabric. The fibers for use in this case are conjugated fibers of core-sheath or side-by-side structure, such as those of PE/PP, PE/PET or PP/PP, treated to be hydrophilic.

In an alternative, the base 11 may be formed from a film of thermoplastic synthetic resin or a laminate sheet of a film and a non-woven fabric. Furthermore, a foam film formed with a large number of holes by applying vacuum to molten/semi-molten resin on a screen drum, or a film formed with holes by elongation strain by hot needles may also be used as the base 11.

When the film formed with holes is used, it is preferred that the diameter of each hole is in a range of 0.5 to 2.0 mm and a rate of hole area is in a range of 5 to 60%. It is also preferred that the film contains whitening inorganic filler such as titanium oxide in a range of 0.5 to 10% by weight.

When the base 11 is formed from the non-woven fabric, wettability may be compensated by blending hydrophilic fibers, such as rayon, natural cellulose fibers or the like to the aforementioned thermoplastic synthetic resin fibers in a content of 5 to 30% by weight.

In the case where the base 11 is formed from the non-woven fabric, the fineness of the thermoplastic synthetic resin fibers is preferably in a range of 1.1 to 4.4 dtex for obtaining both of liquid permeability and fixing strength by thermal fusion with the continuous filament layer 13. For obtaining sufficient fixing strength with the continuous filament layer 13, the fineness of the thermoplastic synthetic resin fibers in the non-woven fabric forming the base 11 is preferably less than or equal to that of the continuous filaments.

On the other hand, the strength of the base 11 greater than or equal to 14.7 N/inch in the Y direction (MD) and greater than or equal to 1.2 N/inch in the X direction (CD) is preferred for obtaining fixing strength with the continuous filament layer 13. Also, the basis weight of the base 11 is preferably in a range of 20 to 40 g/m$^2$.

In a condition shown in FIG. 3, a contracting force is applied to the base 11 in the Y direction by the elastic members 12. By this contracting force, a distance between the fixing lines 14a and a distance between the fixing lines 14b are shortened to form the loop portions 15a and 15b. For uniform strain of the base 11 in the Y direction by elastic contracting force of the elastic members 12, corrugation process is preferably provided for the base 11. Corrugation process is performed by heating two dies, in which ridges and grooves extending in the X direction are repeated at a predetermined pitch in the Y direction, and by clamping the base 11 between them. Thus, the base 11 can be formed with continuous wrinkles of which small ridges and grooves are repeated in the Y direction. If the base 11 is formed with the continuous wrinkles, the wrinkles may be contracted by elastic contracting force of the elastic members 12. Therefore, the base 11 may be uniformly contracted in the Y direction to form the loop portions 15a and 15b of the uniform height between the fixing lines without sacrificing liquid permeability of the base 11.

At the fixing lines 14a and 14b, the base 11 and the continuous filament layer 13 are fusion bonded by heat seal, sonic seal or the like. In the alternative, the base 11 and the continuous filament layer 13 may be bonded with an adhesive at respective fixing lines. In the further alternative, the base 11 and the continuous filament layer 13 may be fixed by using fusion bonding and adhesive bonding together. For the adhesive, use can be made of a pressure-sensitive adhesive. In such case, application amount of the pressure-sensitive adhesive is preferably in a range of 0.5 to 5 g/m$^2$. The line width (thickness) of the fixing lines 14a and 14b is preferably in a range of 0.5 to 5 mm and more preferably in a range of 0.3 to 3 mm. An area ratio of the fixing lines 14a and 14b versus the area of the continuous filament layer 13 is preferably in a range of 3 to 40%, and further preferably in a range of 5 to 25%.

In the first embodiment, the base 1 is preferably formed from the non-woven fabric of the thermoplastic synthetic resin fibers. This non-woven fabric is not stretchable. Accordingly, the elastic members 12 are employed for elastically contracting the base 11 in the Y direction. Each elastic member 12 is made of synthetic rubber or natural rubber and takes form in string or stripe. For providing sufficient contracting force for the base 11 in the Y direction, when strain amount in stretching direction is provided in a range of 5 to 50%, preferred contractive tension of one elastic member is in a range of 1.86 to 7.64 mN. If the preferred range is exceeded, contracting strain of the base 11 in the Y direction becomes excessive to degrade liquid permeability to the absorbent core 8. on the other hand, if the contractive tension is less than the preferred range, sufficient height of the loop portions 15a and 15b cannot be formed.

A pitch of the elastic members 12 in the X direction is preferably in a range of 0.3 to 2 times of the length W of the fixing lines 14a and 14b. The length W of the fixing lines 14a and 14b is preferably in a range of 0.3 to 5 mm. An area ratio of the elastic member 12 versus the area of the region where the loop portions 15a and 15b are formed, is preferably in a range of 3 to 40%. If the preferred range is exceeded, liquid permeability of the base 11 is degraded. On the other hand, if less than the preferred range, sufficient contracting force in the Y direction cannot be applied to the base 11.

FIG. 4 shows one example of a manufacturing process of the surface layer 10 of the absorbent article 1.

A continuous base 11' formed with repeated fine continuous wrinkles by corrugation process is transported by transporting roller group 21. In the transporting roller group 21, rotation speeds of respective rollers are the same. Continuous elastic members 12' are transported by the transporting roller 22 and the transporting roller 23. On the transporting roller group 21, the elastic members 12' are laminated on the lower surface of the base 11'. Upon lamination, an adhesive such as a hot melt adhesive is preliminarily applied on the lower surface of the base 11'. In the alternative, an adhesive such as a hot melt adhesive is preliminarily applied to the elastic members 12'.

Here, rotation speed of the transporting roller 23 is higher than that of the transporting roller 22, and rotation speed of the rollers of the transporting roller group 21 is higher than that of the transporting roller 23. Accordingly, the elastic member 12' is accelerated by these rollers as it is fed so that the elastic members 12' are fitted or laminated on the base 11 in a condition provided tensile strain in a range of 5 to 50%.

On the other hand, a bundle 13B of crimped continuous filaments called as tow, is transported by transporting rollers 24, 25 and 26. Rotation speed of the transporting roller 25 is higher than that of the transporting roller 24, and rotation speed of the transporting roller 26 is lower than that of the transporting roller 25. Accordingly, the bundle 13B of the continuous filaments is stretched between the transporting rollers 24 and 25, and is contracted between the transporting rollers 25 and 26. Stretching stage and contracting stage are repeated for a plurality of times as required, to thereby open the bundle 13B. The bundle 13B thus opened is referred to as a continuous filament layer 13'.

Thereafter, the continuous filament layer 13' is spread (widened) in the X direction by spreading means 29 to have a uniform bulkiness (thickness), and is then stacked on the base 11' through the transporting rollers 27 and 28. Here, since the individual continuous filaments forming the layer 13' are continuously fed, these filaments should be understood to extend substantially in one direction.

A transporting roller 31 is provided on downstream side of the transporting roller group 21. Rotation speed of each roller of the transporting roller group 21 and rotation speed of the transporting roller 31 are the same. Between the transporting roller group 21 and the transporting roller 31, the elastic members 12' are stretched. Therefore, the corrugation of the base 11' is also stretched. Between the transporting roller group 21 and the transporting roller 31, the continuous filament layer 13', the base 11' and the elastic members 12' are clamped by welding rolls 32a and 32b. On one of the welding rolls 32a and 32b, emboss of the fixing line pattern as shown in FIG. 2 is formed. As transported across the welding rolls 32a and 32b, therefore, the continuous filament layer 13' is fixed to the base 11' at the fixing lines 14a and 14b. At this time, the fixing method is heat seal or sonic seal.

At downstream side of the transporting roller 31, stretching force on the elastic members 12' is released. Then, by elastic contracting force of the elastic members 12', the base 11' is uniformly contracted in the Y direction to shorten the distance between the fixing lines 14a and the distance between the fixing lines 14b to form the loop portions 15a and 15b by the continuous filament layer 13'. This resulting laminate is cut into a desired size to form the surface layer 10 having the base 11, the elastic members 12 and the continuous filament layer 13.

In addition to the process illustrated in FIG. 4, there is provided a step of laminating the absorbent core 8 and the surface sheet 9 on the backing sheet 7. The surface layer 10 formed with the loop portions 15a and 15b is supplied on the surface sheet 9 and is bonded thereon by a hot melt adhesive or the like. Thus, the absorbent article 1 shown in FIG. 1 is completed.

In the embodiment shown in FIGS. 1 to 4, the elastic members 12 are laminated on the base 11 so that the base 11 is contracted or shrunken by elastic contracting force of the elastic members 12. However, it is also possible not to provide the elastic member 12 and rather to provide the elastic stretchability for the base 11 per se.

When the base 11 is formed of an elastically stretchable material, the surface layer 10 may be manufactured as following. The continuous base 11' is supplied to the line of FIG. 4 to gradually increase rotation speeds of the transporting rollers, such as the transporting rollers 22, 23 and 21 so that the base 11' may be stretched in the longitudinal direction (feeding direction). Then, on the base 11' in stretched condition, the continuous filament layer 13' is stacked and fixed at respective fixing lines 14a and 14b. Then, the tension force having been applied to the base 11' is released to cause contraction of the base 11' after the laminate is transported across the transporting rollers 31. Thus, loop portions 15a and 15b are formed as set forth above.

As the elastically stretchable base 11, a spunbonded non-woven fabric or meltblown non-woven fabric taking a synthetic rubber as a primary component, may be used. Also, it is preferred to provide perforation process (process for forming openings) for the non-woven fabric. In the alternative, the base 11 formed by providing perforation process for a synthetic rubber type resin film may also be preferred. Here, a non-woven fabric or film formed with a large number of openings is referred to as porous non-woven fabric or film. If openings (holes) are formed in the base 11, the openings may be elongated in the longitudinal direction of the base 11 as it is stretched. Therefore, the base 11 may have high stretchability for exhibiting suitable elastic modulus. With the openings, furthermore, liquid permeability may be enhanced. Preferred diameter of the individual opening is in a range of 0.5 to 2.0 mm, and preferred rate of opening area is in a range of 5 to 60%. When each individual opening is shaped into rhombus or diamond shape, stretchability of the porous film or the porous non-woven fabric can be further improved.

Furthermore, it is also possible to employ a heat shrinkable non-woven fabric or film for the base 11. When such heat shrinkable base 11 is used, the continuous filament layer 13 is stacked on the base 11 under room temperature environment and is fixed at respective fixing lines 14a and 14b. Thereafter, the base 11 is heated to cause heat shrink for forming the loop portions 15a and 15b.

As the heat shrinkable base 11, a porous film applied anisotropic drawing may be used. In the alternative, there may be used a spun laced non-woven fabric formed of conjugated synthetic fibers of core-sheath structure, in which melting point of sheath portion is lower than melting point of core portion. When such non-woven fabric is heated, heat shrinkage strain is caused to the fibers so that overall non-woven fabric is shrunk.

On the other hand, the loop portions may also be formed without using either elastic contraction or thermal construction, by partially contracting (folding) the base 11 with mechanical force after the continuous filament layer 13 is laid over and fixed on the base, and by adhesive bonding or sewing the base at the contracted (folded) portions. In the further alternative, the loop portions may also be formed without contracting the base 11, by stacking the continuous filament layer 13 on the base 11 to have bulges corresponding to the loop portions, and by fixing the layer 13 on the base 11 at fixing portions positioned between adjacent bulges.

FIGS. 5 to 9 are illustrations showing modified patterns of the fixing lines for fixing the continuous filament layer 13 and the base 11.

Figure 5:
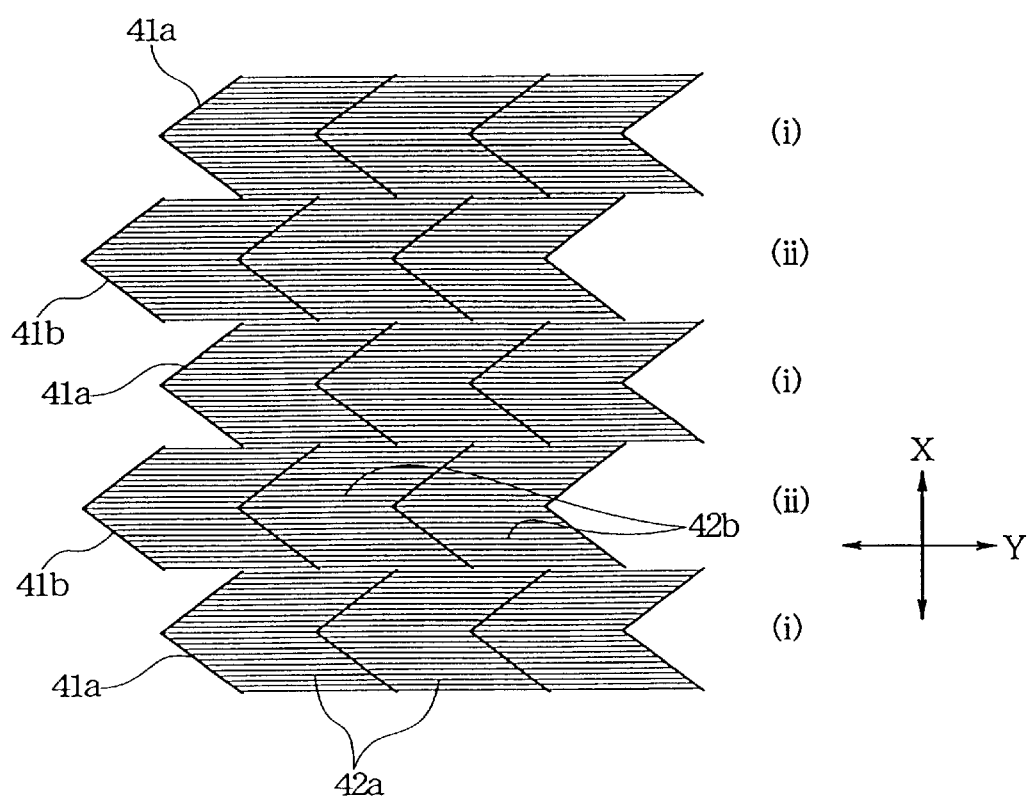
FIG. 5 is a plan view showing a first modification of a pattern of fixing of the continuous filament layer and the base.

In case of the fixing line pattern shown in FIG. 5, fixing lines 41a form odd number rows (i); and fixing lines 41b form even number rows (ii). The fixing lines 41a and 41b are each of V-shape having its corner portion oriented in the Y direction. The distances between adjacent fixing lines 41a are uniform. Between adjacent fixing lines 41a, therefore, there are formed loop portions 42a having a uniform height. Similarly, between adjacent fixing lines 41b, there are formed loop portions 42b having a uniform height.

Figure 6:
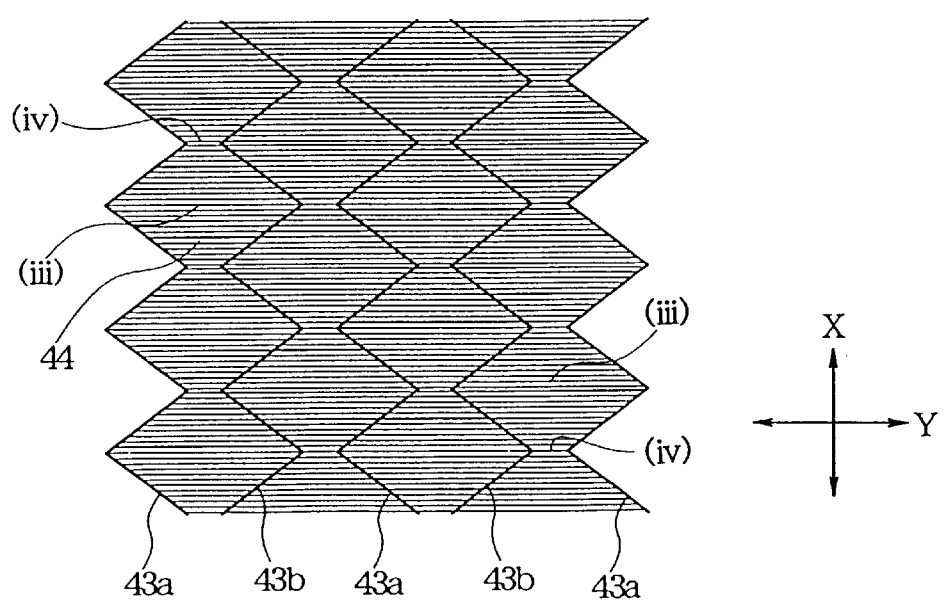
FIG. 6 is a plan view showing a second modification of a pattern of fixing of the continuous filament layer and the base.

In case of the fixing line pattern shown in FIG. 6, fixing lines 43a and 43b tilted in mutually opposite directions are aligned in the X direction to form zigzag pattern and alternately arranged in the Y direction. Between adjacent fixing lines 43a and 43b, there are formed wide regions (iii) and narrow regions (iv) alternating in the X direction. Therefore, the height of loop portions 44 formed between adjacent fixing lines 43a and 43b is large at the center portions in the wide regions (iii) and is gradually decreased to the narrow regions (iv).

Since the height varies over different portions of the loop portion 44, the continuous filaments are movable in the X direction and Y direction with freedom, at the highest portions of the loop portions. Also, since the loop portions have the largest height at the center portions in the regions (iii), the contact area between the loop portions and the wearer's skin becomes so small as to provide soft feeling.

Figure 7:
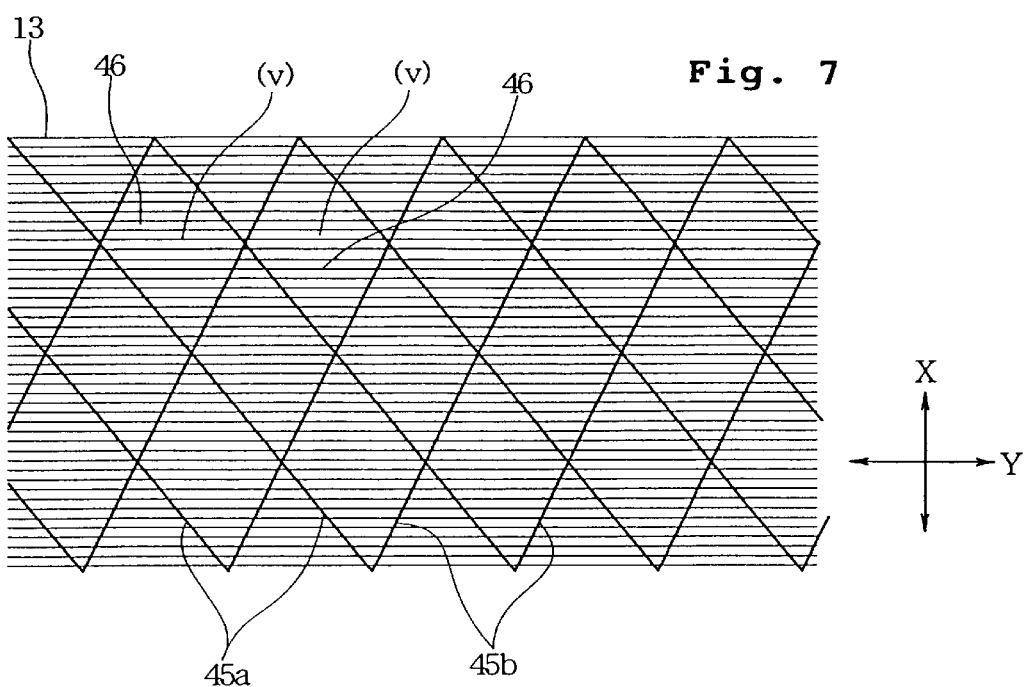
FIG. 7 is a plan view showing a third modification of a pattern of fixing of the continuous filament layer and the base.

In case of the fixing line pattern shown in FIG. 7, there are formed fixing lines 45a and 45b obliquely extending in straight with opposite tilting directions, and regions (v) defined by the fixing lines 45a and 45b are mutually independent with each other. In each of the independent regions (v), a loop portion 46 of the continuous filament layer 13 is formed. The distance between mutually opposing fixing lines 45a and 45b is the largest at the center portion of the region (v) and is gradually narrowed toward the extreme where the opposing fixing lines 45a and 45b intersects. Therefore, in each region (v), the height of the loop portion 46 is the largest at the center portion and is gradually decreased toward the ends in the X direction.

Figure 8:
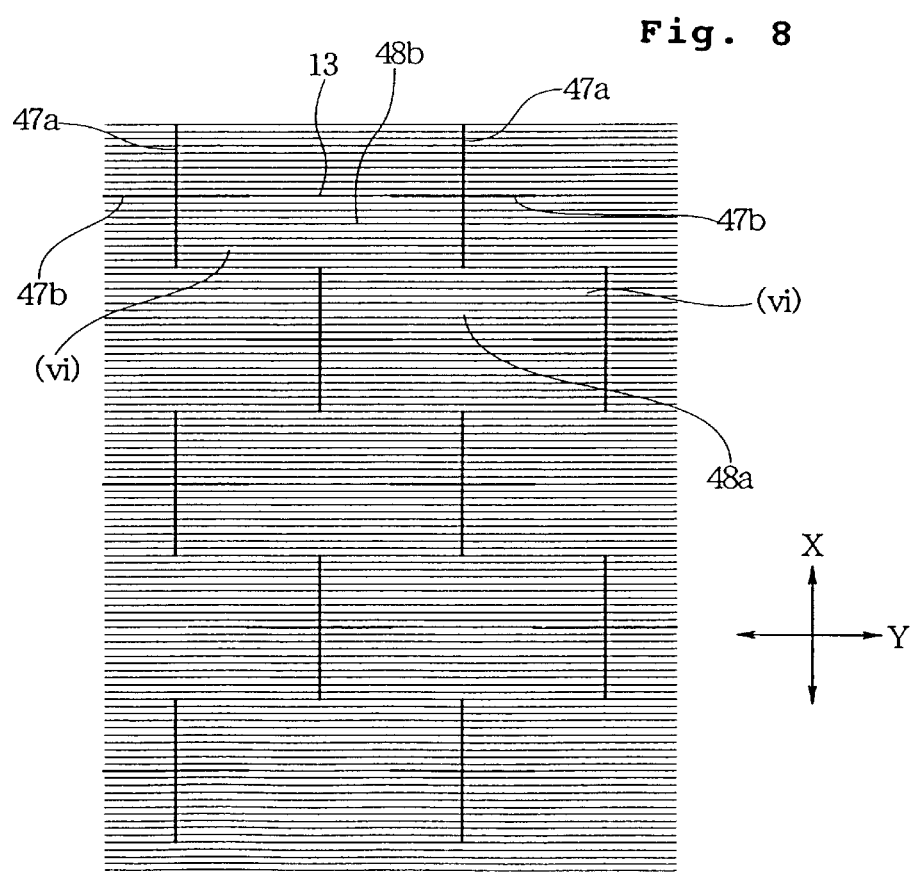
FIG. 8 is a plan view showing a fourth modification of a pattern of fixing of the continuous filament layer and the base.

In case of the fixing line pattern shown in FIG. 8, fixing lines 47a extending in the X direction and fixing lines 47b extending in the Y direction are formed to intersect crosswise. Regions (vi) are defined by the fixing lines and are arranged alternately. In the regions (vi), the loop portions 48a and 48b are formed between the fixing lines 47a in such a manner that peaks of the loop portions 48a and 48b are positioned alternately. Thus, the continuous filaments forming respective loop portions 48a and 48b can behave independently of each other.

Figure 9:
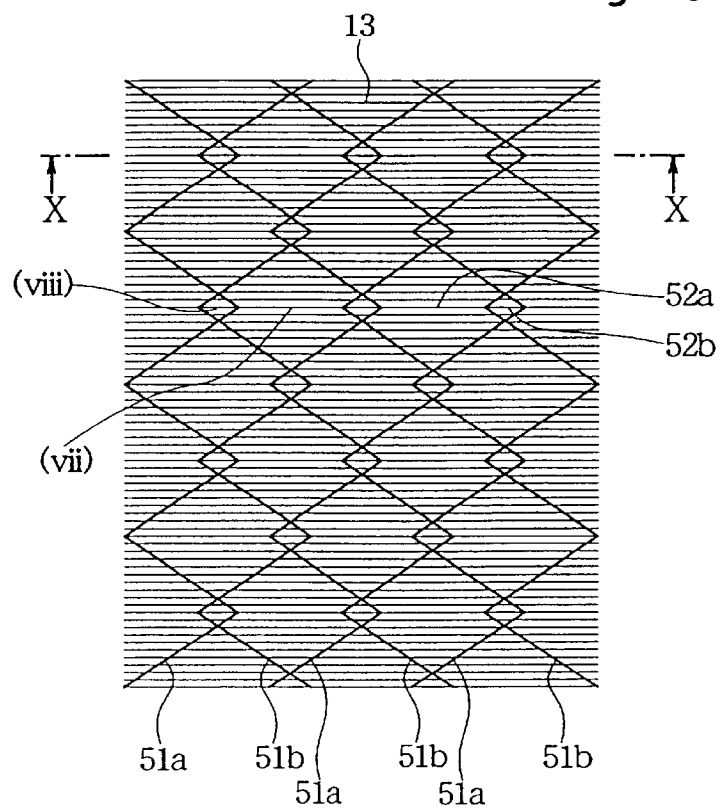
FIG. 9 is a plan view showing a fifth modification of a pattern of fixing of the continuous filament layer and the base.

In case of the fixing line pattern shown in FIG. 9, fixing lines 51a and 51b tilted in mutually opposite directions are aligned in the X direction to form zigzag pattern and alternately arranged in the Y direction while being overlapped. Thus, large area regions (vii) and small area regions (viii) are formed in the portions surrounded by the fixing lines 51a and 51b.

Figure 10:
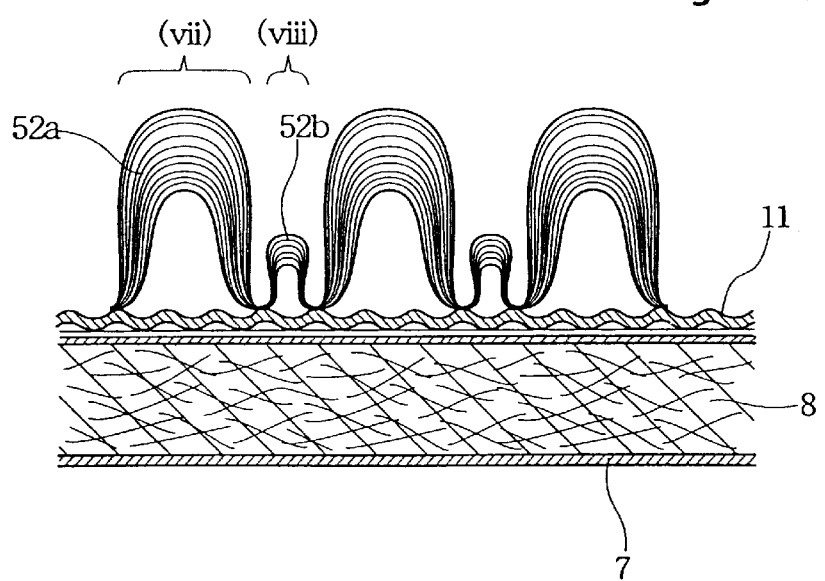
FIG. 10 is a section taken along line X—X of FIG. 9.

FIG. 10 is a section taken along line X—X of FIG. 9. As can be seen from the section in FIG. 10, a loop portion 52a having a greater height is formed in the region (vii), and a loop portion 52b having a smaller height is formed in the region (viii). The greater height loop portions 52a and the smaller height loop portions 52b are formed alternately. Also, even in the respective regions (vii) and (viii), the height of the loop varies over different portions.

Since the greater height loop portions and the smaller height loop portions are formed in admixing manner, the surface layer provides soft feeling on the wearer's skin. Moreover, the smaller height loop portions contribute for achieving good liquid permeability to the absorbent core 8.

Figure 11:
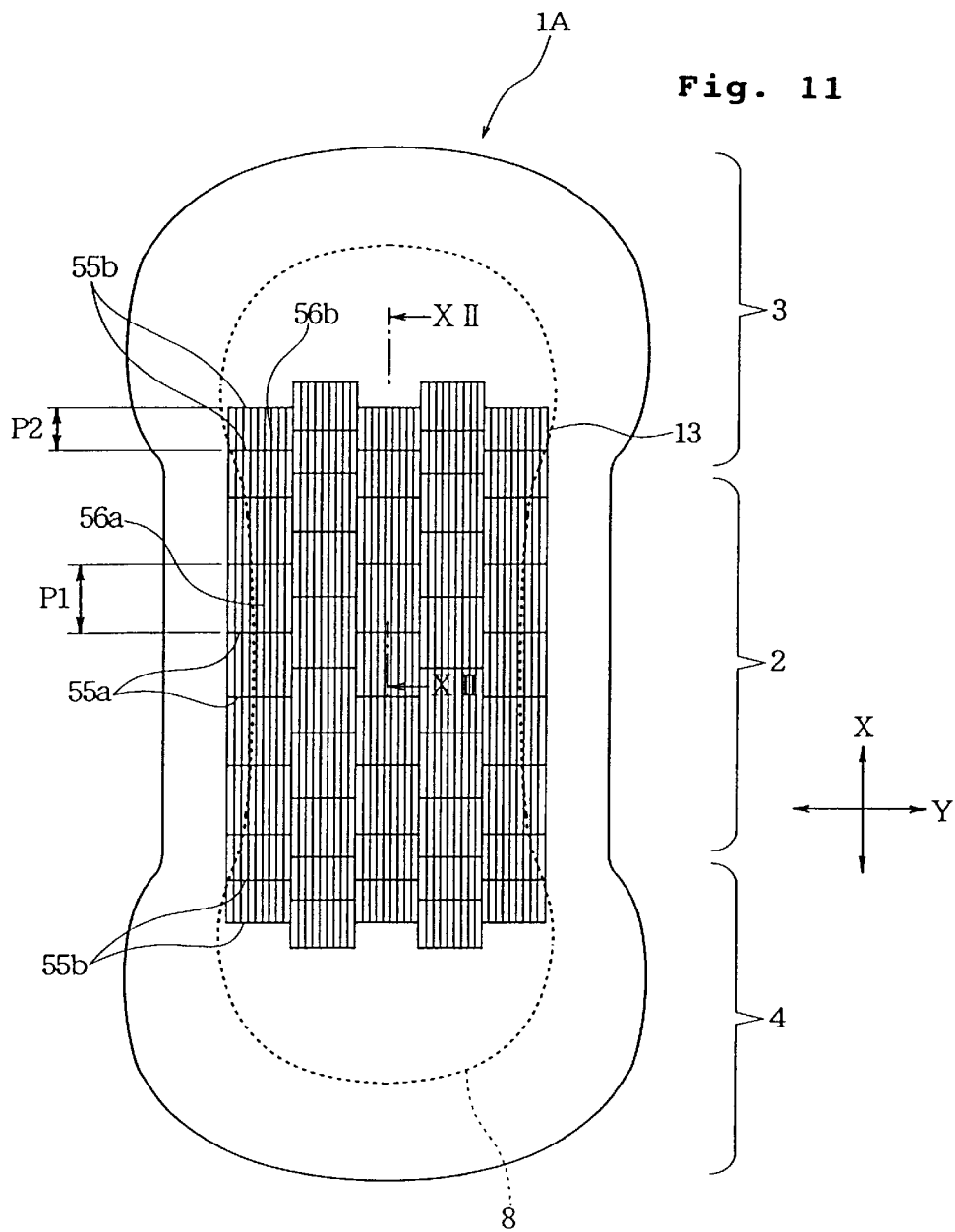
FIG. 11 is a plan view of an absorbent article according to a second embodiment of the present invention.
Figure 12:
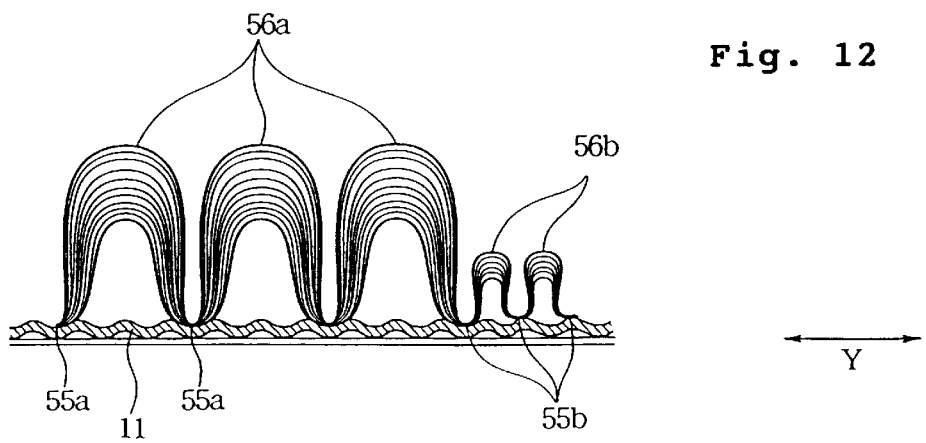
FIG. 12 is a section of a surface layer taken along line XII—XII of FIG. 11.

FIG. 11 is a plan view showing an absorbent article 1A according to a second embodiment of the present invention, and FIG. 12 is a section taken along line XII—XII of FIG. 11, schematically showing a portion of a surface layer of the absorbent article 1A. Hereinafter, the detailed description of the portions having substantially the same constructions as those of the first embodiment will be omitted by designating them by the common reference numerals.

In the absorbent article 1A, the continuous filament layer 13, of which continuous filaments extend in the longitudinal direction (Y direction), is fixed to the base 11 at fixing lines. Here, fixing lines arranged with a wider pitch P1 in the intermediate portion 2, namely at least in the center portion of the liquid absorbing region, are indicated at 55a; and fixing lines arranged with a narrower pitch P2 in the front and rear portions are indicated at 55b.

As a result, as shown in FIG. 12, loop portions 56a having a greater height are formed between the fixing lines 55a at the center portion, and loop portions 56b having a smaller height are formed between the fixing lines 55b at the front and rear sides of the center portion. It should be noted that it is also possible to set the pitch of fixing lines along both the lateral (left and right) sides smaller than that of fixing lines at the center portion between the lateral sides so that the loop portions at both the lateral sides may have a smaller height than the loop portions at the center portion.

In the center portion for receiving a large amount of liquid, the greater height loop portions 56a are formed from the continuous filament layer 13. Therefore, re-wetting back from the absorbent core 8 can be successfully suppressed owing to presence of the loop portions 56a. On the other hand, in the front and rear portions and occasionally in both of left and right side portions where the amount of liquid to be applied is relatively small, the smaller height loop portions 56b are formed. Even in these portions, the continuous filaments may move freely to achieve soft feeling.

Figure 13:
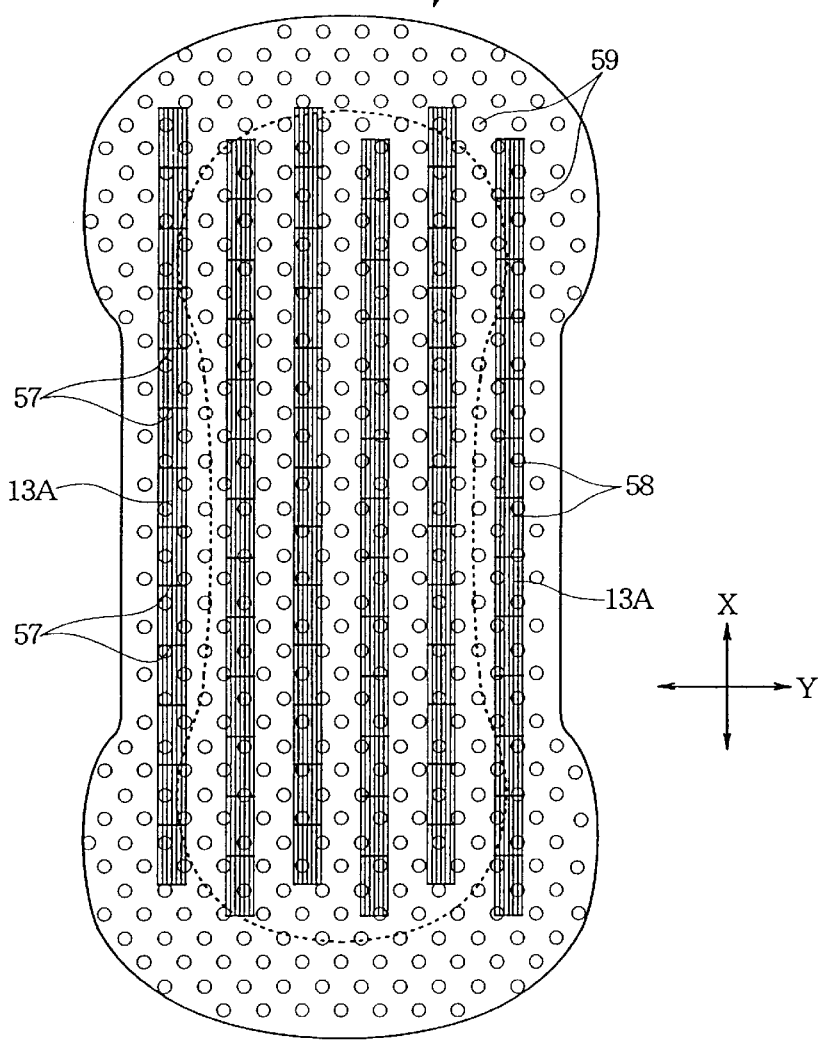
FIG. 13 is a plan view of an absorbent article according to a third embodiment of the present invention.
Figure 14:
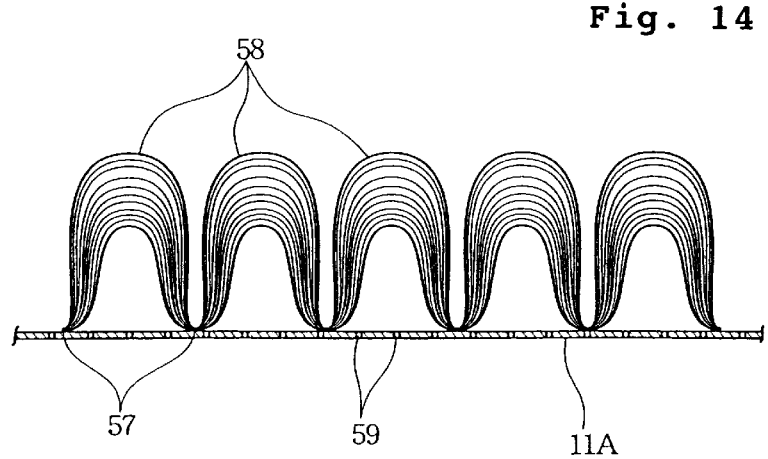
FIG. 14 is a section of a surface layer of the absorbent article shown in FIG. 13.

FIG. 13 is a plan view showing an absorbent article 1B according to a third embodiment of the present invention, and FIG. 14 is a partial section of a surface layer thereof.

In the absorbent article 1B, a predetermined width of strips of a continuous filament layer 13A are provided on the surface of a base 11A formed of a film or non-woven fabric having openings (through holes) 59. These strips of the continuous filament layer 13A extend in parallel in the Y direction and are spaced apart in the X direction. The continuous filament layer 13A is fixed on the base 11A at fixing lines 57. Between fixing lines 57, loop portions 58 of the continuous filament layer 13A are formed.

In the shown embodiment, the loop portions 58 formed of the band-shaped strips of the continuous filament layer 13A contact with the wearer's skin, and the continuous filaments move following to motion of the wearer's skin to be less irritative. When a liquid is applied to the loop portions 58, it flows along the continuous filaments in the loop portions 58 to be given to the base 11A, and then to reach the absorbent core 8 through the openings 59. Between adjacent strips of the continuous filament layer 13A, on the other hand, a liquid can be directly applied to the base 11A to pass through the openings 59 to be absorbed in the absorbent core 8. Thus, good liquid permeability can be achieved.

EXAMPLES

Example

The surface layer 10 having structure shown in FIGS. 1 to 3 was manufactured in the following manner.

(Continuous Filament Layer 13)

As the continuous filaments, used were core-sheath type conjugated synthetic fibers of PE/PP, having a fineness of 6.6 dtex, number of crimp by mechanical crimping process being 18 per inch, an elastic restoration ratio of 84%, a single yarn strength of 31.4 mN/dtex, containing titanium oxide of 2% by weight, and having hydrophilic oil of 0.3% by weight deposited on the surface.

The basis weight of the continuous filament layer 13 was adjusted to be 70 g/m$^2$.

(Base 11)

As the base, a spunbonded non-woven fabric having a basis weight of 20 g/m$^2$ was used. Used fibers were core-sheath type conjugated fibers with core of PP and sheath of PE, with a fineness of 2.2 dtex and a fiber length of 51 mm.

A breaking strength of the base 11 in the Y direction (MD) was 19.9 N/inch, and a breaking strength of the base 11 in the X direction (CD) was 6.5 N/inch.

For the base 11, corrugation process was applied for forming wrinkles by a die, in which ridges and grooves extending in the X direction were repeated in the Y direction. The die had a height of 1 mm from the bottom of the groove to the peak of the ridge and a ridge and groove repetition pitch was 0.35 mm.

(Elastic Member 12)

As the elastic members 12, used were polyurethane elastic yarns of 155 dtex. These elastic yarns were so fixed on the base 11 while being stretched three times in the Y direction, as to extend in parallel in the Y direction and to be spaced apart in the X direction at a pitch of 7 mm. For fixing the elastic yarns, a hot melt adhesive was used. In the condition where the elastic members 12 were fixed on the base 11 and the elastic members 12 were stretched for three times of original yarn length, the contracting force per one inch width to be exerted on the base 11 was 1.4 N.

(Fixing Lines 14a and 14b)

The fixing line pattern was identical to that shown in FIG. 2, in which the fixing lines 14a and 14b were staggered between the odd number rows (i) and even number rows (ii). The line width (width in the Y direction) of each individual fixing line was 0.5 mm, and the length W in the X direction was 5 mm. In the condition where the elastic members 12 were stretched for three times of the original length, the pitch P of the fixing lines 14a was 15 mm and the pitch P of the fixing lines 14b was also 15 mm. The individual fixing lines 14b were each located at the exact mid-point between adjacent fixing lines 14a. At a timing where the fixing lines were formed (before releasing the tension on the elastic members 12), the area ratio of the fixing lines was 3.3%.

The fixing lines were formed by fusion bonding (welding) the continuous filament layer 13 and the base 11. This fusion bond was performed by sonic seal using an embossing die.

(Loop Portions 15a and 15b)

In a condition where the tension on the elastic members 12 was released and the base 11 was contracted in the Y direction, the pitch P of the fixing lines 14a in the Y direction was 5 mm and the pitch P of the fixing lines 14b in the Y direction was also 5 mm. Then, the loop portions 15a and 15b of the height H of 6 mm from the surface of the base 11 were formed.

Comparative Example

As comparative example of the surface layer to be compared with the example set forth above, the following through-air bonded non-woven fabric was used.

Used fibers were core-sheath type conjugated fibers of PE/PP, having a fineness of 2.2 dtex and a fiber length of 51 mm. Basis weight of the non-woven fabric was 25 g/m².

<Evaluation>

(1) Checking of Freedom of Continuous Filament (Displacement)

By means of a handy digital force gauge (NITTO DEN-SAN SHINPO K.K.) having a probe of 10 mmφ the surfaces of the example and the comparative example were pushed in the X direction, Y direction and Z direction perpendicular to X-Y plane to measure moving distance of the probe at a time where the pushing force (measured value) exceeds 0.2 N. Result is shown in the following table 1.

TABLE 1

|  | X direction | Y direction | Z direction |
| --- | --- | --- | --- |
| Example | 10 mm | 5 mm | 6 mm |
| Comparative | 0 mm | 0 mm | 0 mm |

(Load)

By means of a handy digital force gauge (NITTO DEN-SAN SHINPO K.K.) having a probe of 10 mmφ the surfaces of the example and the comparative example were pushed in the X direction, Y direction and Z direction perpendicular to X-Y plane to measure pushing load when the probe is moved in amount of 5 mm. The result is shown in the following table 2.

TABLE 2

|  | X direction | Y direction | Z direction |
| --- | --- | --- | --- |
| Example | 34.3 mN | 58.8 mN | 39.2 mN |
| Comparative | not moved for 5 mm | not moved for 5 mm | not moved for 5 mm |

(Bulk Restoration Ability)

Thickness (A) was measured in a condition applied no load in the Z direction, and subsequently, a pressure of 3430 Pa was applied for 10 minutes, thereafter thickness (B) was measured after removal of pressure for deriving a compression restoration ratio (=(B/A)×100 (%)). The result is shown in the following table 3.

TABLE 3

|  | Compression Restoration Ratio |
| --- | --- |
| Example | 78.6% |
| Comparative | 80.9% |

(2) Checking of Absorbing Ability

On a PA film, there was laid an absorbent layer, in which pulp and superabsorbent polymer were blended. Then, on the absorbent layer, the surface layers of the example and comparative example were placed for measurement of absorbing ability.

As artificial menstrual blood for evaluation, red colored solution containing mainly glycerin and having viscosity of 23 cps as measured by Vismetron (single cylinder type rotational viscometer: SIBAURA SYSTEMS CO., LTD), was used.

(Penetration Period)

Upon dripping 3 g of artificial menstrual blood at discharge rate of 90 g/min from the above, a period to penetrate the artificial menstrual blood from the interface of the surface layer of the example and the comparative example to the absorbent layer was measured. The result is shown in the following table 4.

TABLE 4

|  | Penetration Period |
| --- | --- |
| Example | 2.5 seconds |
| Comparative | 3.3 seconds |

(Re-wetting Back)

7 g of artificial menstrual blood was dripped from the above at discharge rate of 7 g/min and thereafter left for 1 minute. Thereafter, a filter paper of weight Cg was placed on the surface layer. Then, by placing an acrylic plate on the filter paper, and by placing a weight on the acrylic plate, 3420 Pa of pressure was applied. After expiration of 3 minutes, weight Dg of the filter paper was measured. Then, re-wetting back ratio (%)={(D×C)/7}×100 was measured. The result is shown in the following table 5.

TABLE 5

|  | Re-wetting Back Rate |
|---|---|
| Example | 12.5% |
| Comparative | 16.1% |

(3) Fixing Strength of Continuous Filament and Base

The surface layer of the example was cut into 1 inch width. Then, by means of AUTOGRAPH (SHIMADZU CO.: AGS-1KNG), the loop portion was gripped by one chuck and the base was gripped by the other chuck to perform peeling off test at a speed of 100 mm/min. The maximum load was 0.6 N.

In the absorbent article according to the present invention, as has been described above, the surface layer is provided with the loop portions of the continuous filaments. Therefore, it can follow movement of the skin of a wearer so as not to irritate the skin. Also, the absorbent article can achieve superior liquid permeability and can prevent re-wetting back.

Although the present invention has been illustrated and described with respect to exemplary embodiment thereof, it should be understood by those skilled in the art that the foregoing and various other changes, omission and additions may be made therein and thereto, without departing from the spirit and scope of the present invention. Therefore, the present invention should not be understood as limited to the specific embodiment set out above but to include all possible embodiments which can be embodied within a scope encompassed and equivalent thereof with respect to the feature set out in the appended claims.

What is claimed is:

1. A manufacturing process of an absorbent article having a surface layer, a backing sheet, and an absorbent layer interposed between said surface layer and said backing sheet, comprising the steps of:

(a) fitting a longitudinally stretched elastic member over one surface of a liquid permeable base;

(b) simultaneously with the step (a) or before or after the step (a), stacking a layer of continuous filaments extending substantially in one direction on the other surface of said base and fixing the continuous filament layer to said base at a plurality of fixing portions which are spaced apart in the filament extending direction by a given initial pitch;

(c) causing contraction of said base in the filament extending direction to shorten said given initial pitch into a given contracted pitch by releasing stretching force on said elastic member for raising said continuous filaments in each region between adjacent fixing portions from the surface of said base to form loop portions, and whereby forming said surface layer; and (d) laminating said surface layer, said backing sheet on opposite surfaces of said absorbent layer for forming said absorbent article;

wherein the base is corrugated prior to step (a) so as to have wrinkles that are repeated in the filament extending direction.

2. The manufacturing process as set forth in claim 1, which further comprises a step of opening a tow which is a bundle of crimped continuous filaments for forming said continuous filament layer.

3. The manufacturing process as set forth in claim 2, which further comprises a step of spreading said continuous filament layer in its width direction to have a uniform bulk, after the step of opening.

* * * * *